(12) United States Patent
Vortman et al.

(10) Patent No.: US 8,251,908 B2
(45) Date of Patent: Aug. 28, 2012

(54) MOTION COMPENSATED IMAGE-GUIDED FOCUSED ULTRASOUND THERAPY SYSTEM

(75) Inventors: Jacob Vortman, Haifa (IL); Yoav Medan, Haifa (IL); Benny Assif, Ramat Hasharon (IL)

(73) Assignee: Insightec Ltd., Tiret Carmel (IL)

( * ) Notice: Subject to any disclaimer, the term of this patent is extended or adjusted under 35 U.S.C. 154(b) by 993 days.

(21) Appl. No.: 11/865,662

(22) Filed: Oct. 1, 2007

(65) Prior Publication Data

US 2009/0088623 A1    Apr. 2, 2009

(51) Int. Cl.
*A61B 8/00* (2006.01)
(52) U.S. Cl. ........ 600/439; 600/407; 600/437; 600/441; 601/2
(58) Field of Classification Search .................. 600/407, 600/410, 411, 420, 421, 422, 423, 424, 415; 606/34; 601/2; 324/315, 314, 309, 312, 324/322
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,942,150 A | 3/1976 | Booth et al. |
| 3,974,475 A | 8/1976 | Burckhardt et al. |
| 3,992,693 A | 11/1976 | Martin et al. |
| 4,000,493 A | 12/1976 | Spaulding et al. |
| 4,074,564 A | 2/1978 | Anderson |
| 4,206,653 A | 6/1980 | Lemay |
| 4,339,952 A | 7/1982 | Foster |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,662,222 A | 5/1987 | Johnson |
| 4,858,597 A | 8/1989 | Kurtze et al. |
| 4,865,042 A | 9/1989 | Umemura et al. |

(Continued)

FOREIGN PATENT DOCUMENTS

DE        4345308 C2    2/2001

(Continued)

OTHER PUBLICATIONS

International Search Report and Written Opinion for PCT/IB2008/003069—actual completion date of Apr. 2, 2009 (11 pages).

(Continued)

*Primary Examiner* — Brian Casler
*Assistant Examiner* — Joel Lamprecht
(74) *Attorney, Agent, or Firm* — Bingham McCutchen LLP (57) ABSTRACT

An image-guide therapy system comprises a thermal treatment device (e.g., an ultrasound transducer) configured for transmitting a therapeutic energy beam, and The system further comprises an imaging device (e.g., a magnetic resonant imaging (MRI) device) configured for acquiring images of the target tissue mass and the thermal treatment device. The system further comprises a controller configured for controlling thermal dose properties of the thermal treatment device to focus the energy beam on a target tissue mass located in an internal body region of a patient, and a processor configured for tracking respective positions of the thermal treatment device and the target tissue mass in a common coordinate system based on the acquired images. The system may optionally comprise a display configured for displaying the acquired images.

14 Claims, 6 Drawing Sheets

U.S. PATENT DOCUMENTS

| | | |
|---|---|---|
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 5,209,221 A | 5/1993 | Riedlinger |
| 5,211,160 A | 5/1993 | Talish et al. |
| 5,247,935 A | 9/1993 | Cline et al. |
| 5,271,400 A | 12/1993 | Dumoulin et al. |
| 5,275,165 A | 1/1994 | Ettinger et al. |
| 5,291,890 A | 3/1994 | Cline et al. |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,339,282 A | 8/1994 | Kuhn et al. |
| 5,368,031 A | 11/1994 | Cline et al. |
| 5,368,032 A | 11/1994 | Cline et al. |
| 5,379,642 A | 1/1995 | Reckwerdt et al. |
| 5,391,140 A | 2/1995 | Schaetzle et al. |
| 5,413,550 A | 5/1995 | Castel |
| 5,435,312 A | 7/1995 | Spivey et al. |
| 5,443,068 A | 8/1995 | Cline et al. |
| 5,474,071 A | 12/1995 | Chapelon et al. |
| 5,485,839 A | 1/1996 | Aida et al. |
| 5,490,840 A | 2/1996 | Uzgiris et al. |
| 5,507,790 A | 4/1996 | Weiss |
| 5,520,188 A | 5/1996 | Hennige et al. |
| 5,526,814 A | 6/1996 | Cline et al. |
| 5,549,638 A | 8/1996 | Burdette |
| 5,553,618 A | 9/1996 | Suzuki et al. |
| 5,557,438 A | 9/1996 | Schwartz et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,722,411 A | 3/1998 | Suzuki et al. |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,810,008 A | 9/1998 | Dekel et al. |
| 5,831,739 A | 11/1998 | Ota |
| 5,873,845 A | 2/1999 | Cline et al. |
| 5,897,495 A | 4/1999 | Aida et al. |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,023,636 A | 2/2000 | Wendt et al. |
| 6,042,556 A | 3/2000 | Beach et al. |
| 6,071,239 A | 6/2000 | Cribbs et al. |
| 6,113,559 A | 9/2000 | Klopotek |
| 6,128,522 A | 10/2000 | Acker et al. |
| 6,128,958 A | 10/2000 | Cain |
| 6,193,659 B1 | 2/2001 | Ramamurthy et al. |
| 6,242,915 B1 | 6/2001 | Hurd |
| 6,246,896 B1 * | 6/2001 | Dumoulin et al. ............ 600/411 |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boernert et al. |
| 6,322,527 B1 | 11/2001 | Talish |
| 6,334,846 B1 | 1/2002 | Ishibashi et al. |
| 6,374,132 B1 * | 4/2002 | Acker et al. .................. 600/411 |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,532 B1 | 8/2002 | Doukas et al. |
| 6,461,314 B1 | 10/2002 | Pant et al. |
| 6,475,150 B2 | 11/2002 | Haddad |
| 6,478,739 B1 | 11/2002 | Hong |
| 6,506,154 B1 | 1/2003 | Ezion et al. |
| 6,506,171 B1 | 1/2003 | Vitek et al. |
| 6,511,428 B1 | 1/2003 | Azuma et al. |
| 6,522,142 B1 | 2/2003 | Freundlich |
| 6,523,272 B1 | 2/2003 | Morales |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,824,516 B2 | 11/2004 | Batten et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 * | 12/2006 | Halperin et al. ............... 600/411 |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,452,357 B2 * | 11/2008 | Vlegele et al. .................. 606/32 |
| 7,462,488 B2 | 12/2008 | Madsen et al. |
| 7,505,805 B2 * | 3/2009 | Kuroda ...................... 600/410 |
| 7,505,808 B2 | 3/2009 | Anderson et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 2001/0031922 A1 | 10/2001 | Weng et al. |
| 2002/0035779 A1 | 3/2002 | Krieg et al. |
| 2002/0082589 A1 | 6/2002 | Friedman et al. |
| 2002/0188229 A1 | 12/2002 | Ryaby |
| 2003/0004439 A1 | 1/2003 | Pant et al. |
| 2003/0060820 A1 | 3/2003 | Maguire et al. |

| | | | |
|---|---|---|---|
| 2003/0187371 A1 | 10/2003 | Vortman et al. | |
| 2004/0030227 A1* | 2/2004 | Littrup et al. | 600/300 |
| 2004/0030251 A1 | 2/2004 | Ebbini et al. | |
| 2004/0068186 A1 | 4/2004 | Ishida et al. | |
| 2004/0122323 A1 | 6/2004 | Vortman et al. | |
| 2004/0199068 A1* | 10/2004 | Bucholz et al. | 600/411 |
| 2004/0210134 A1 | 10/2004 | Hynynen et al. | |
| 2004/0236253 A1 | 11/2004 | Vortman et al. | |
| 2004/0267126 A1 | 12/2004 | Takeuchi | |
| 2005/0033201 A1 | 2/2005 | Takahashi et al. | |
| 2005/0096542 A1 | 5/2005 | Weng et al. | |
| 2005/0131301 A1 | 6/2005 | Peszynski et al. | |
| 2005/0203444 A1 | 9/2005 | Schonenberger et al. | |
| 2005/0251046 A1 | 11/2005 | Yamamoto et al. | |
| 2006/0052661 A1 | 3/2006 | Gannot et al. | |
| 2006/0052701 A1 | 3/2006 | Carter et al. | |
| 2006/0052706 A1 | 3/2006 | Hynynen et al. | |
| 2006/0058671 A1 | 3/2006 | Vitek et al. | |
| 2006/0058678 A1 | 3/2006 | Vitek et al. | |
| 2006/0079773 A1 | 4/2006 | Mourad et al. | |
| 2006/0106300 A1 | 5/2006 | Seppenwoolde et al. | |
| 2006/0173385 A1 | 8/2006 | Lidgren et al. | |
| 2006/0184069 A1 | 8/2006 | Vaitekunas | |
| 2006/0206105 A1 | 9/2006 | Chopra et al. | |
| 2006/0229594 A1 | 10/2006 | Francischelli et al. | |
| 2007/0016013 A1 | 1/2007 | Camus | |
| 2007/0016039 A1 | 1/2007 | Vortman et al. | |
| 2007/0055140 A1 | 3/2007 | Kuroda | |
| 2007/0066897 A1 | 3/2007 | Sekins et al. | |
| 2007/0073135 A1 | 3/2007 | Lee et al. | |
| 2007/0098232 A1 | 5/2007 | Matula et al. | |
| 2007/0167781 A1 | 7/2007 | Vortman et al. | |
| 2007/0197918 A1 | 8/2007 | Vitek et al. | |
| 2007/0219470 A1 | 9/2007 | Talish et al. | |
| 2008/0027342 A1 | 1/2008 | Rouw et al. | |
| 2008/0031090 A1 | 2/2008 | Prus et al. | |
| 2008/0033278 A1 | 2/2008 | Assif | |
| 2008/0082026 A1 | 4/2008 | Schmidt et al. | |
| 2008/0108900 A1 | 5/2008 | Lee et al. | |
| 2008/0183077 A1 | 7/2008 | Moreau-Gobard et al. | |
| 2008/0228081 A1 | 9/2008 | Becker et al. | |
| 2008/0249408 A1 | 10/2008 | Palmeri et al. | |
| 2008/0292194 A1 | 11/2008 | Schmidt et al. | |
| 2008/0312562 A1 | 12/2008 | Routh et al. | |
| 2009/0088623 A1 | 4/2009 | Vortman et al. | |
| 2010/0056962 A1 | 3/2010 | Vortman et al. | |
| 2011/0034800 A1 | 2/2011 | Vitek et al. | |

FOREIGN PATENT DOCUMENTS

| | | |
|---|---|---|
| EP | 1132054 A1 | 9/2001 |
| EP | 0151073 | 11/2005 |
| EP | 1774920 A1 | 4/2007 |
| EP | 1790384 | 5/2007 |
| FR | 2806611 A1 | 9/2001 |
| JP | 11313833 A | 11/1999 |
| WO | WO-9100059 A1 | 1/1991 |
| WO | WO-9852465 A1 | 11/1998 |
| WO | WO-0031614 A1 | 6/2000 |
| WO | WO-0158337 | 8/2001 |
| WO | WO-0166189 A1 | 9/2001 |
| WO | WO-0180709 A2 | 11/2001 |
| WO | WO-02058791 A1 | 8/2002 |
| WO | WO-03/013654 A1 | 2/2003 |
| WO | WO-03097162 A2 | 11/2003 |
| WO | WO-03098232 A2 | 11/2003 |
| WO | WO-2004093686 | 11/2004 |
| WO | WO-2005058029 A2 | 6/2005 |
| WO | WO-2006018837 A2 | 2/2006 |
| WO | WO-2006025001 A1 | 3/2006 |
| WO | WO-2006087649 A1 | 8/2006 |
| WO | WO-2006119572 | 11/2006 |
| WO | WO-2007073551 A1 | 6/2007 |
| WO | WO-2008039449 | 4/2008 |
| WO | WO-2008050278 A1 | 5/2008 |
| WO | WO-2008075203 A2 | 6/2008 |
| WO | WO-2008119054 A1 | 10/2008 |
| WO | WO-2009/044276 | 4/2009 |
| WO | WO-2009055587 A1 | 4/2009 |
| WO | WO-2009094554 | 7/2009 |
| WO | WO-2011/015949 | 2/2011 |

OTHER PUBLICATIONS

Cline, H.E., et al., "MR Temperature Mapping of Focused Ultrasound Surgery", Magnetic Resonance in Medicine, Academic Press, Duluth, MN, US, vol. 32, No. 6, 1 Kiem 1994 (Jun. 1, 1994), ISSN: 0740-3194, p. 628, figure 6.

Cain, C. and Umemura, S., "Concentric-Ring and Sector-Vortex Phased-Array Applicators for Ultrasound Hyperthermia," IEEE Transactions on Microwave Theory and Techniques, vol. MTT-34, No. 5, pp. 542-551 (May 1986).

Fjield, T. and Hynynen, K., The Combined Concentric-Ring and Sector-Vortex Phased Array for MRI Guided Ultrasound Surgery, IEEE Transactions on Ultrasonics, Ferroelectrics and Frequency Control, vol. 44, No. 5, pp. 1157-1167 (Sep. 1997).

Baudouin Denis de Senneville, Charles Mougenot, Chrit T.W. Moonen. Real-Time Adaptive Methods for Treatment of Mobile Organs by MRI-Controlled High-Intensity Focused Ultrasound. Magnetic Resonance in Medicine 57: 319-330 (2007), Wiley-Liss, Inc.

McGough, et al., "Direct Computation of Ultrasound Phased-Array Driving Signals from a Specified Temperature Distribution for Hyperthermia," IEEE Trans. On Biomedical Engineering, vol. 39, No. 8, pp. 825-835 (Aug. 1992).

International Preliminary Report on Patentability mailed on Apr. 15, 2010 for International Application No. PCT/IB2008/003069 (10 pages).

McDannold, et al., "Quality Assurance and System Stability of a Clinical MRI-guided focused ultrasound system: Four-year experience," Medical Physics, vol. 33, No. 11, pp. 4307-4313 (Oct. 2006).

Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).

Chen et al., "MR Acoustic Radiation Force Imaging: Comparison of Encoding Gradients."

Cline et al., "Focused US system for MR imaging-guide tumor ablation," Radiology, v. 194, No. 3, pp. 731-738 (Mar. 1995).

Cline et al., "Simultaneous magnetic resonance phase and magnitude temperature maps in muscle," Magnetic Resonance in Medicine, vol. 35, no. 3, pp. 309-315 (Mar. 1996).

Daum et al., "Design and evaluation of a feedback based phased array system for ultrasound surgery," IEEE Trans. Ultrason. Ferroelec. Freq. Control, vol. 45, No. 2, pp. 431-434 (1998).

Herbert et al., "Energy-based adaptive focusing of waves: application to ultrasonic transcranial therapy," 8th Intl. Symp. On Therapeutic Ultrasound.

Huber et al., "A New Noninvasive Approach in Breast Cancer Therapy Using Magnetic Resonance Imaging-Guided Focussed Ultrasound Surgery," Cancer Research 61, 8441-8447 (Dec. 2001).

International Preliminary Report on Patentability in International Patent Application No. PCT/IB2004/001512, mailed Dec. 8, 2005.

International Search Report and Written Opinion in International Patent Application No. PCT/IB2004/001498, dated Aug. 31, 2004.

International Search Report and Written Opinion in International Patent Application No. PCT/IB2005/002273, mailed Dec. 20, 2005.

International Search Report and Written Opinion in International Patent Application No. PCT/IB2005/002413, mailed Nov. 22, 2005.

International Search Report and Written Opinion in International Patent Application No. PCT/IB2006/001641, mailed Sep. 25, 2006.

International Search Report and Written Opinion in International Patent Application No. PCT/IB2006/003300, mailed Feb. 14, 2008.

International Search Report and Written Opinion in International Patent Application No. PCT/IB2007/001079, mailed Dec. 10, 2007.

International Search Report and Written Opinion in International Patent Application No. PCT/IB2007/002134, mailed Dec. 13, 2007.

International Search Report and Written Opinion in International Patent Application No. PCT/IB2007/002140, mailed Dec. 29, 2008.

Jolesz et al., "Integration of interventional MRI with computer-assisted surgery," J. Magnetic Resonance Imaging. 12:69-77 (2001).

Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).

Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).

Maxwell et al., "Noninvasive thrombolysis using pulsed ultrasound cavitation therapy—Histotripsy," Abstract, U.S. Natl. Lib. Of Med., NIH, Ultrasound Med. Biol. (Oct. 23, 2009).

McDannold et al., "MRI evaluation of thermal ablation of tumors and focused ultrasounds," JMRI vol. 8, No. 1, pp. 91-100 (1998).

McDannold et al., "Magnetic resonance acoustic radiation force imaging," Med. Phys. vol. 35, No. 8, pp. 3748-3758 (Aug. 2008).

Medel et al., "Sonothrombolysis: An emerging modality for the management of stroke," Neurosurgery, vol. 65, No. 5, pp. 979-993.

Mougenot et al., "MR monitoring of the near-field HIFU heating," 8th Intl. Symp. On Therapeutic Ultrasound, edited by E.S. Ebbini, U. of Minn. (Sep. 2009).

Partial International Search Report and Written Opinion in International Patent Application No. PCT/IB2007/001079, dated Sep. 25, 2007.

Vimeux et al., "Real-time control of focused ultrasound heating based on rapid MR thermometry," Investig. Radiology, vol. 43, No. 3, pp. 190-193.

Vykhodtseva et al., "MRI detection of the thermal effects of focused ultrasound on the brain," Ultrasound in Med. & Biol., vol. 26, No. 5, pp. 871-880 (2000).

Written Opinion in International Patent Application No. PCT/IL01/00340, mailed Feb. 24, 2003.

Written Opinion in International Patent Application No. PCT/IL02/00477, mailed Feb. 25, 2003.

Written Opinion in International Patent Application No. PCT/IB03/05551, mailed Sep. 10, 2004.

"How is Ablatherm treatment performed?" http://www.edap-hifu.com/eng/physicians/hifu/3c_treatment_treat-description.htm, accessed Jan. 3, 2003.

"What is HIFU? HIFU: High Intensity Focused Ultrasound," http://www.edap-hifu.com/eng/physicians/hifu2a_hifu_overview.htm, accessed Jan. 3, 2003.

"What are the physical principles?" http://www.edap-hifu.com/eng/physicians/hifu/2c_hifu_physical.htm, accessed Jan. 3, 2003.

"How does HIFU create a lesion?" http://www.edap-hifu.com/eng/physicians/hifu/2d_hifu_lesion.htm, accessed Jan. 3, 2003.

"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.

"Abstract" Focus Surgery, http://www.focus-surgery.com/Sanghvi.htm, accessed Jan. 3, 2003.

Exablate 2000 Specification, InSightec, Ltd. (2 pages).

FDA Approves Exablate 2000 as Non-invasive surgery for Fibroids, Oct. 22, 2004.

International Search Report and Written Opinion in International Patent Application No. PCT/IB2010/000189, mailed Jun. 1, 2010.

International Search Report for PCT/IB03/05551 completion date Mar. 2, 2004 (5 pages).

International Search Report and Written Opinion in International Patent Application No. PCT/IB2010/000971, mailed Jul. 29, 2010 (9 pages).

Office Action mailed Dec. 26, 2011 for Chinese Patent Application No. 200880109807.1 (translation) 13 pages.

* cited by examiner

MOTION COMPENSATED IMAGE-GUIDED FOCUSED ULTRASOUND THERAPY SYSTEM

FIELD OF THE INVENTION

The present invention relates to thermal treatment systems, and more particularly, to image-guided focused ultrasound therapy systems.

BACKGROUND OF THE INVENTION

Thermal energy, such as generated by high intensity focused ultrasound (acoustic waves with a frequency greater than about 20 KHz, and more typically between 50 KHz and 5 MHz), may be used to therapeutically treat internal tissue within a patient. For example, ultrasonic waves may be used to ablate tumors (e.g., breast tumors and uterine fibroids), thereby obviating the need for invasive surgery. For this purpose, a phased transducer array having transducer elements driven by electrical signals to produce ultrasonic energy can be placed external to the patient, but in close proximity to the target tissue mass to be ablated.

The transducer is geometrically shaped and positioned, such that the ultrasonic energy is focused at a "focal zone" corresponding to the target tissue mass within the patient. During the wave propagation across tissue, a portion of the ultrasound energy is absorbed, leading to increased temperature and eventually to cellular necrosis, preferably at the target tissue mass at the focal zone. The focal zone of the transducer can be rapidly displaced by independently adjusting the amplitude and phase of the electrical signal input to each of the transducer elements. The focal size and focal length of the ultrasound transducer will depend on the ultrasound frequency, the focal depth and the aperture size of the transducer. Because the size of target tissue mass is often greater than the size of the focal zone, the transducer may be sequentially focused and activated at a number of target sites within the target tissue mass to fully coagulate the target volume. The sequential "sonications" are used to cause coagulation necrosis of an entire tissue structure, such as a tumor, of a desired size and shape.

Image-guided focused ultrasound therapy systems offer the benefit of target visualization and localization. In particular, before a focused ultrasound treatment procedure is performed, a patient may be initially imaged to localize the mass and/or to plan a trajectory of the ultrasound beam. For example, using displayed images of the internal body region, a treatment boundary can be defined around the target tissue mass, and obstacle boundaries can be defined around tissue that should not be exposed to the ultrasound energy beam. The ultrasound transducer can then be operated based on these defined boundaries. During treatment, the patient can be continuously imaged to ensure that the target tissue mass is treated without damaging surrounding healthy tissue.

Magnetic Resonance Imaging (MRI) guidance offers the additional benefit of temperature mapping in vivo, which can be used to verify that a sufficient temperature is reached during each application of ultrasonic energy (i.e., sonication) to kill the target tissue mass or portion thereof. Temperature mapping can be accomplished by measuring the temperature change (rise) of the portion of the tissue mass being heated during each sonication using conventional MR imaging techniques coupled with image processing to extract the temperature from the MRI data. Thus, accurate temperature measurements allow verification of the proper location of the focal zone and computation of the accumulated thermal dose during treatment for prediction of tissue ablation.

Current image-guided focused ultrasound therapy systems, such as those based on MRI, assume that the acoustic transducer is in a predefined and known position relative to the target tissue mass to be treated. In this case, the respective coordinate systems defined by the imaging device, therapeutic device, and patient remain registered with each other. If unplanned movement of either the transducer or the patient is detected, however, one or both of these coordinate systems become mis-registered with the other coordinate systems. As such, the treatment process must be stopped and the ultrasound beam trajectory re-planned. This introduces significant inefficiencies in the treatment process and may generate significant delays. Some image-guided focused ultrasound therapy systems use mechanically aligned imaging and ultrasound transducer arrangements or use the same transducer to perform both imaging and therapy tasks. In these cases, the coordinates of the therapy system remain registered with the coordinates of the imaging system if the transducer moves. However, if the patient moves, the patient coordinate system in which the target tissue region is defined, will become mis-registered with the imaging and therapeutic coordinate systems.

Current generation of systems require that all three coordinate systems—patient, imaging, and therapeutic, be locked or be continually registered with respect to each other, so that treatment of the target tissue region without damaging surrounding healthy tissue can be assured and verified. Conventionally, this has been accomplished by mechanically aligning the imaging and therapy transducers, as briefly discussed above, and immobilizing the target tissue region. However, electronic phasing changes or electrical impedance changes within the control circuitry of the transducer may still generate misalignment between the imaging and therapy beams; that is, cause mis-registration between the imaging and therapeutic coordinate systems. In addition, immobilization of the target tissue region of the patient may not always be practically accomplished.

For example, after delivery of a thermal dose, e.g., an ultrasound sonication, a cooling period is required to avoid harmful and painful heat build up in healthy tissue adjacent the target tissue mass. This cooling period may be significantly longer than the thermal dosing period. Since a large number of sonications may be required in order to fully treat the target tissue mass, the overall time required can be quite significant. This means that the patient must remain motionless in the imaging device for a significant period of time, which can be very stressful. At the same time, it may be critical that the entire target tissue mass be ablated (such as, e.g., in the case of a malignant cancer tumor), and that no short cuts be taken during the procedure just in the name of patient comfort. Thus, the use of image-guided focused therapy systems are limited to treating tissue masses with small motion amplitudes or to those that are easily immobilized.

Recently, it has been suggested that the movement of a target tissue mass relative to an MRI device and ultrasound transducer can be compensated for when the motion is periodic (e.g., motion caused by a physiological cycle, such as a cardiac or respiratory cycle). See Denis de Senneville, B., Mougenot, C., and Moonen, C., Real-Time Adaptive Methods for Treatment of Mobile Organs by MRI-Controlled High-Intensity Focused Ultrasound, Magnetic Resonance in Medicine 57:319-330 (2007). In particular, an MRI of a target tissue mass currently acquired during a treatment procedure can be compared to reference MRI images of the target tissue mass previously acquired during a periodic cycle before the treatment procedure, which information can then be used to predict the displacement of the target tissue mass relative to the MRI device and ultrasound transducer. The ultrasound beam generated by the transducer can then be electronically controlled in real-time to continually maintain its focal zone at the moving target tissue mass. While this technique may be successful when tracking a target tissue mass that moves in accordance with a periodic cycle, it does not address non-periodic movement of the target tissue mass; for example, when the patient moves within the imaging device.

There, thus, remains a need for an improved method and system that can correlate relative displacement between an imaging device, a therapeutic device, and a target tissue mass in real time.

SUMMARY OF THE INVENTION

In accordance with a first aspect of the present inventions, an image-guide therapy system is provided. The system comprises a thermal treatment device configured for transmitting a therapeutic energy beam. In one embodiment, the thermal treatment device is an external thermal treatment device configured for transcutaneously transmitting the energy beam into a patient. In another embodiment, the thermal treatment device is an ultrasound transducer, in which case, the energy beam will be an ultrasound energy beam. For example, the ultrasound transducer may comprise a multiplicity of independently controlled transducer elements, and the thermal dose properties may be controlled by adjusting the one or more of a phase, frequency, and amplitude of respective drive signals supplied to the respective transducer elements. The system further comprises an imaging device (e.g., a magnetic resonance imaging (MRI) device) configured for acquiring images of the target tissue mass and the thermal treatment device. In one embodiment, the thermal treatment device and imaging device are different devices, although the thermal treatment device and imaging device can be the same device.

The system further comprises a controller configured for controlling thermal dose properties of the thermal treatment device to focus the energy beam on a target tissue mass located in an internal body region of a patient, and a processor configured for tracking respective positions of the thermal treatment device and the target tissue mass in a common coordinate system (e.g., a three-dimensional coordinate system) based on the acquired images. The system may optionally comprise a display configured for displaying the acquired images.

In one embodiment, the processor is configured for tracking the respective positions of the thermal treatment device and the target tissue mass during non-periodic relative movement between the thermal treatment device and the target tissue mass. The respective positions of the thermal treatment device and the target tissue mass may be tracked in any one of a variety of manners. For example, the processor may be configured for tracking the respective positions of the thermal treatment device and the target tissue mass by analyzing fiducial markers associated with one or both of the thermal treatment device and the target tissue mass within the acquired images, by transmitting or receiving signals to or from a localization element associated with one or both of the thermal treatment device and the target tissue mass, or by comparing the acquired images with one or more reference images.

The tracked positions of the thermal treatment device and the target tissue mass can be used in any one of a variety of manners. For example, the controller may be configured for automatically adjusting one or more of the thermal dose properties of the thermal treatment device (e.g., by adjusting electrical and/or mechanical parameters of the thermal treatment device) based on the tracked positions of the thermal treatment device and the target tissue mass to compensate for a change in the relative position between the thermal treatment device and the target tissue mass. In this example, the system may optionally comprise a user interface configured for allowing a system operator to define a treatment boundary of the target tissue mass using the acquired images, in which case, the controller may be configured for automatically controlling the thermal dose properties of the thermal treatment device to focus the energy beam within the defined treatment boundary of the target tissue mass. The user interface may also be configured for allowing the system operator to define an obstacle boundary of tissue, in which case, the controller can be further configured for controlling the thermal dose properties of the thermal treatment device to avoid traversing the defined obstacle boundary with the energy beam. As another example, the processor may be configured for tracking treated regions and untreated regions of the target tissue mass based on the tracked positions of the thermal treatment device and the target tissue mass.

In accordance with a second aspect of the present inventions, another image-guide therapy system is provided. The system comprises a thermal treatment device configured for transmitting a therapeutic energy beam having a focal zone, and an imaging device configured for acquiring images of the target tissue mass. The thermal treatment device and imaging device may have the same features described above. The system further comprises a controller configured for controlling thermal dose properties of the thermal treatment device to locate the focal zone of the energy beam coincident with a target tissue mass located in an internal body region of a patient, and a processor configured for tracking relative non-periodic movement between the focal zone of the energy beam and the target tissue mass in real-time based on the acquired images. The system may optionally comprise a display configured for displaying the acquired images.

In one embodiment, the relative non-periodic movement between the focal zone of the energy beam and the target tissue mass is tracked in a common three-dimensional coordinate system. In another embodiment, the processor is configured for tracking the relative non-periodic movement between the focal zone of the energy and the target tissue mass in a common three-dimensional coordinate system. The relative non-periodic movement between the focal zone of the energy beam and the target tissue mass can be tracked in any one of a variety of manners. For example, the respective positions of the thermal treatment device and the target tissue mass may be tracked during non-periodic relative movement between the thermal treatment device and the target tissue mass using any one of the exemplary techniques described above, or if the acquired images are thermally sensitive images, the thermal signature of the focal zone of the energy beam within the thermally sensitive images can be analyzed.

The tracked relative non-periodic movement between the thermal treatment device and the target tissue mass can be used in any one of a variety of manners, including those described above. For example, the controller may be configured for automatically adjusting one or more of the thermal dose properties of the thermal treatment device (e.g., by adjusting electrical and/or mechanical parameters of the thermal treatment device) based on the tracked relative non-periodic movement between the focal zone of the energy beam and the target tissue mass to compensate for a change in the relative position between the thermal treatment device and the target tissue mass. In this example, the system may optionally comprise a user interface having the same functions described above. As another example, the processor may be configured for tracking treated regions and untreated regions of the target tissue mass based on the tracked relative non-periodic movement between the thermal treatment device and the target tissue mass.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
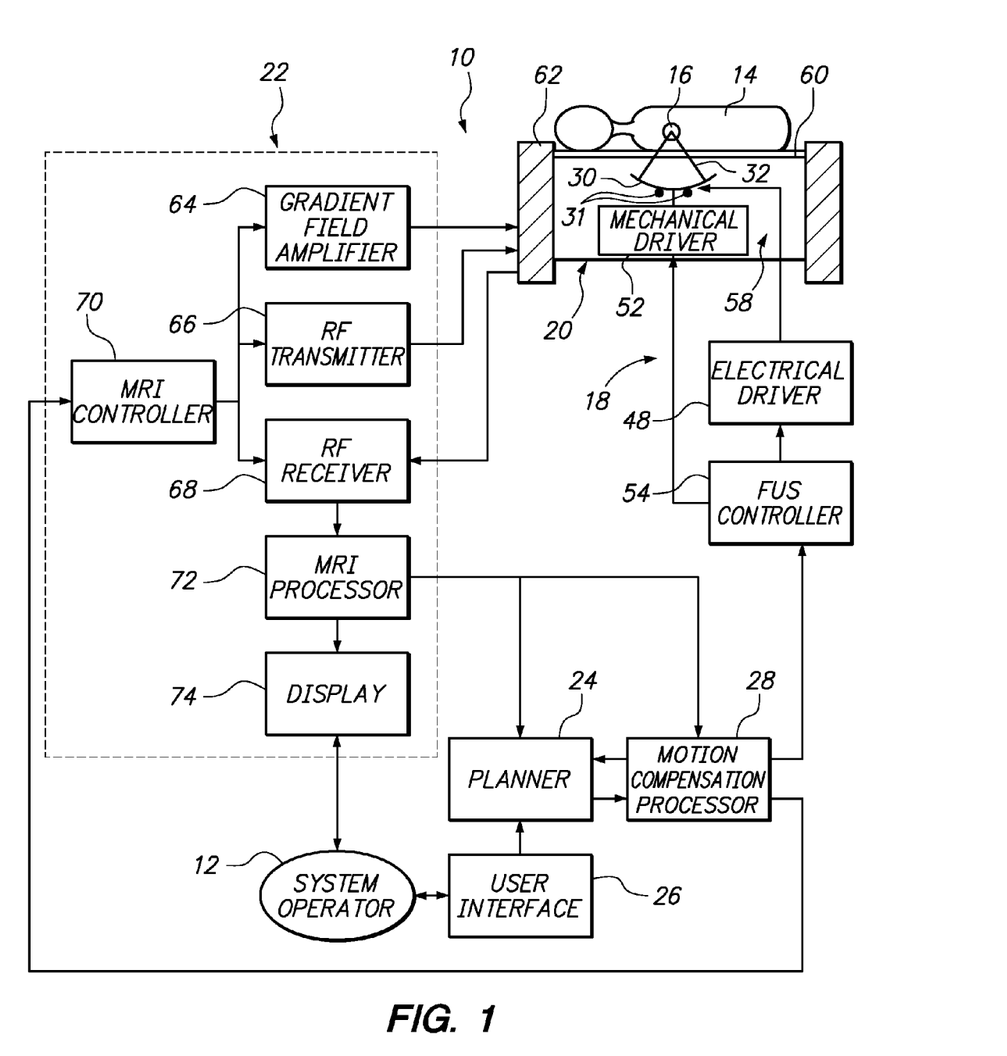
FIG. 1 is a block diagram of an image-guided therapy system constructed in accordance with one embodiment of the present inventions.

Referring generally to FIG. 1, an image-guided therapy system 10 arranged in accordance with one embodiment of the present inventions will now be described. The system 10 is designed to be operated by a system operator 12 to treat a target tissue mass 16 (e.g., a tumor) within an internal body region of a patient 14. The system 10 generally comprises a focused thermal treatment subsystem 18, a patient table 20, an imaging subsystem 22, a planner 24, a user interface 26, and a motion compensation processor 28. It should be noted that the elements illustrated in FIG. 1 are functional in nature, and are not meant to limit the structure that performs these functions in any manner. For example, several of the functional blocks can be embodied in a single device, or one of the functional blocks can be embodied in multiple devices. Also, the functions can be performed in hardware, software, or firmware.

Figure 2:
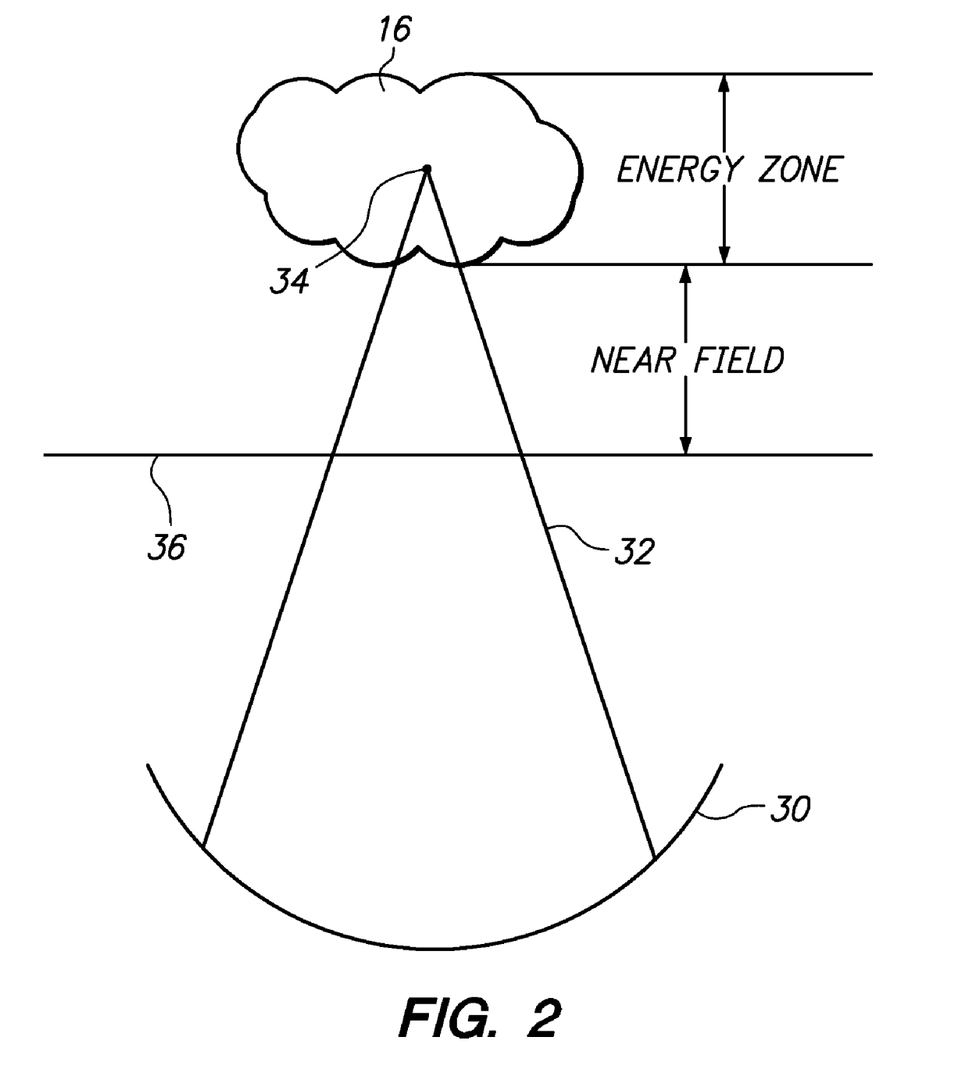
FIG. 2 is a plan view of an ultrasound transducer used in the system of FIG. 1 to treat a target tissue mass located in the interior region of a patient.

Referring further to FIG. 2, the thermal treatment system 12 comprises a thermal treatment device 30 configured for delivering an energy beam 32 to the target tissue mass 16 within the patient 14. The energy beam 32 raises the temperature of the target tissue mass 16 by transferring the power of the energy beam as heat to the target tissue mass 16. The energy beam 32 is focused on the target tissue mass 16 in order to raise the temperature of the target tissue mass 16 to a point where it is destroyed. The heat distribution within the tissue is controlled by the energy density within a focal zone 34 of the energy beam 32, the tissue acoustic parameters and, to some extent, the duration of the energy beam application. In the illustrated embodiment, the thermal treatment device 30 is configured for being placed external to the patient 14, in which case, the energy beam 32 will be transcutaneously transmitted into the patient 14, so that the energy beam 32 is focused on the target tissue mass 16 some distance from a skin surface 36 of the patient 14. The distance from the skin surface 36 to the target tissue mass 16 is the near field, which contains healthy tissue. It is important that tissue in the near field is not damaged by the energy beam 32. Thus, the energy beam 32 is preferably focused within the target zone, where the energy is transferred as heat to the target tissue mass 16.

Figure 3:
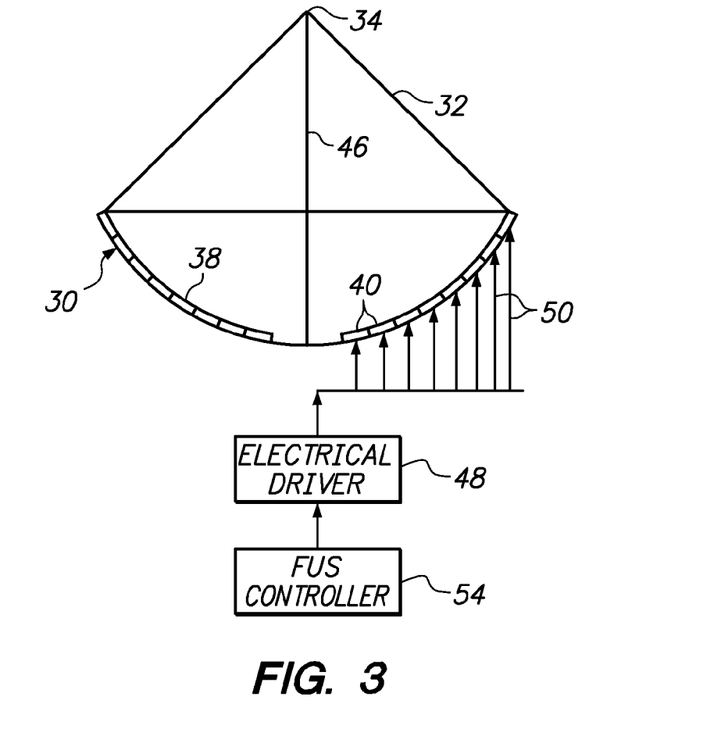
FIG. 3 is a cross-section view of the ultrasound transducer of FIG. 2 being controlled by electrical drive signals.
Figure 4A:
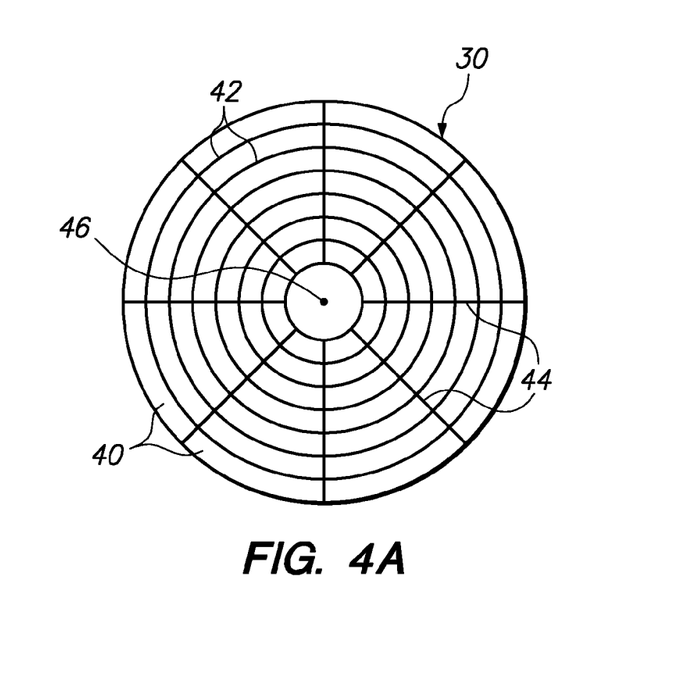
FIG. 4A is a top view of one embodiment of the ultrasound transducer of FIG. 2
Figure 4B:
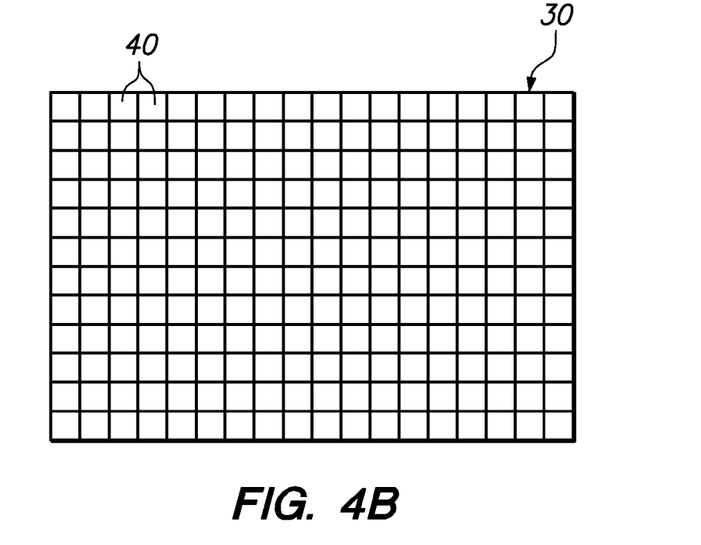
FIG. 4B is a top view of an alternative embodiment of the ultrasound transducer of FIG. 2.

In one implementation illustrated in FIGS. 3 and 4A, the thermal treatment device 30 takes the form of a phased array ultrasound transducer, in which case, the energy beam 32 takes the form of an ultrasound energy beam. In one embodiment, the transducer 30 may have a concave or bowl shape, such as a "spherical cap" shape; that is, having a substantially constant radius of curvature, such that the transducer 30 has an inside surface 38 defining a portion of a sphere. Alternatively, as illustrated in FIG. 4B, the transducer 30 may have a substantially flat configuration and/or may include an outer perimeter that is generally rectangular. It should be appreciated that a variety of geometric designs for the transducer 30 may be employed. Additionally, alternative embodiments of the system 10 may use focused radiators, acoustic lenses, or acoustic reflectors in order to achieve optimal focus of the beam 32. In a preferred embodiment, the transducer 30 has an outer diameter of between about two and sixteen centimeters.

The ultrasound transducer 30 converts an electronic drive signal (described in further detail below) into acoustic power in the ultrasound beam 32. In particular, the ultrasound transducer 30 comprises a plurality of transducer elements 40, each composed of piezoelectric material or other materials like silicon-based transducers, such that, upon being driven with a sinusoidal signal near the resonant frequency of the piezoelectric material or silicon transducers, the transducer elements 40 vibrate according to the phase and amplitude of the exciting sinusoidal signal, thereby creating the desired ultrasound energy beam 32.

The exemplary embodiment of the transducer 30 is divided radially into six concentric rings 42 and circumferentially into eight sectors 44 disposed about a central axis 46, thereby dividing the transducer 30 into forty eight transducer elements 40. Alternatively, the transducer 30 may be divided into any desired number of rings 42 and/or sectors 44. In the illustrated embodiment, each transducer element 40 has an arcuate shape, although each transducer element 40 may have any one or more of a variety of geometric shapes, such as hexagons, triangles, squares, and the like. In the illustration FIG. 4B, a different implementation is described in which the array is flat with very large number of elements isotropically spread over the surface. The configuration of the transducer 14, however, is not important to the present invention, and any of a variety of known ultrasound transducers may be used, such as flat circular arrays, linear arrays, and the like. Additional information on the construction of an ultrasound transducer appropriate for use with the system 10 may be found, for example, in Cain, C. and Umemura, S., "Concentric-Ring and Sector-Vortex Phased-Array Applicators for Ultrasound Hyperthermia," IEEE Transactions on Microwave Theory and Techniques, Vol. MTT-34, No. 5, pages 542-551 (May 1986); and Fjield, T. and Hynyen, K., "The Combined Concentric-Ring and Sector-Vortex Phased Array for MRI Guided Ultrasound Surgery, IEEE Transactions on Ultrasonics, Ferroelectrics, and Frequency Control, Vol. 44, No. 5, pages 1157-1167 (September 1997), the disclosures of which are expressly incorporated herein by reference.

The thermal treatment subsystem 18 further comprises an electrical driver 48 to which each of the transducer elements 40 is individually coupled in a conventional manner. The electrical driver 48 is configured for providing electrical drive signals 50 to the transducer elements 40 at one or more frequencies, preferably at radio frequencies (RF), for example, from 0.25 MHz to 10 MHz, and more preferably from 0.5 MHz to 3.0 MHz. When electrical drive signals 50 are provided to the transducer elements 40, the transducer 30 emits ultrasonic energy from its inner surface 38 as is known to those skilled in the art.

Referring specifically now to FIG. 1, the thermal treatment subsystem 18 further comprises a mechanical driver 52 (or positioner) that is coupled to the transducer 30. In one embodiment, the mechanical driver 52 may be operated to translate with the transducer 30 in a plane that is perpendicular to the axis of the transducer 30, as well as controlling the roll and pitch of the transducer 30. A preferred mechanical driver (or positioner) is disclosed in U.S. Pat. No. 6,582,381, entitled "Mechanical Positioner for MRI Guided Ultrasound Therapy System," which is expressly incorporated herein by reference.

The thermal treatment subsystem 18 further comprises a focus ultrasound (FUS) controller 54 that controls the thermal dose properties of the transducer 30 via the electrical driver 48 and the mechanical driver 52. Thermal dose properties may include the duration and power of the ultrasound beam 32, the frequency of the acoustic beam, and the position and size of the focal zone 34 of the ultrasound beam 32. In order to control the thermal dose properties of the transducer 30, the FUS controller 54 is coupled to the electrical driver 48 to dictate the electrical parameters (e.g., amplitude, frequency, and/or phase and duration) of the drive signals 50 (shown in FIG. 3), and thus the electrical parameters of the ultrasound energy emitted by the respective transducer elements 40. For example, the FUS controller 54 may control the amplitude of the drive signals 50 to control the intensity of ultrasonic energy delivered by the transducer 30, and the phase and frequency of the drive signals 50 to control the location, shape and size of the focal zone 34 and/or to adjust the focal distance (which in essence is a subset of location) of the focal plane (i.e., the distance from the face of the transducer 30 to the center of the focal zone 34). The frequency of the drive signals 50 can also be adjusted to optimize the energy density within the focal zone 34. To provide for precise positioning and dynamic movement and reshaping of the focal zone 34, it is desirable to be able to adjust the phase and/or amplitude of the individual transducer elements 40 relatively quickly, e.g., in the microsecond range. In order to further control the thermal dose properties of the transducer 30, and in particular, the position of the focal zone 34, the FUS controller 54 is also coupled to the mechanical driver 52, so that the mechanical position of the transducer 30 can be adjusted to displace the focal zone 34 to a desired location.

More advanced techniques for obtaining specific focal distances and shapes are disclosed in U.S. Pat. No. 6,506,171, entitled "Systems and Methods for Controlling Distribution of Acoustic Energy Around a Focal Point Using a Focused Ultrasound System," U.S. Pat. No. 6,419,648, entitled "Systems and Methods for Reducing Secondary Hot Sports in a Phase Array Focused Ultrasound System," and U.S. Pat. No. 6,613,004, entitled "Systems and Methods for Creating Longer Necrosed Volumes Using a Phased Array Focused Ultrasound System," all of which are expressly incorporated herein by reference.

Significantly, as will be described in further detail below, the FUS controller 54, based on information supplied by the motion compensation processor 28, automatically controls the electrical and mechanical properties of the transducer 30 based on a tracked relative movement between the focal zone 34 of the ultrasound beam 32 and the target tissue mass 16 to maintain the location of the focal zone 34 of the ultrasound energy beam 32 inside the target tissue mass 16. In one embodiment, the FUS controller 54 automatically controls the electrical and mechanical properties of the transducer 30 based on tracked positions of the transducer 30 and the target tissue mass 16 to compensate for any change in the relative position between the therapy device and the target tissue mass.

Referring still to FIG. 1, the patient table 56 comprises a chamber 58 filled with degassed water or similar acoustically transmitting fluid in which the transducer 30 is disposed. Alternatively, the chamber 58 may be disposed in a fluid-filled bag mounted on a movable arm that may be placed against the patient's body (not shown). The patient table 56 further comprises a flexible membrane 60 on which the patient 14 may be disposed. That membrane 60 is composed of a material that is substantially transparent to ultrasound, such as Mylar®, polyvinyl chloride (PVC), or other suitable plastic material. A fluid-filled bag (not shown) may be provided on the membrane 60 that may conform easily to the contours of the patient 14 disposed on the table 56, thereby acoustically coupling the patient 14 to the transducer 30 within the chamber 58. In addition or alternatively, an acoustic gel, water, or other fluid (not shown) may be provided between the patient 14 and the membrane 60 to facilitate further acoustic coupling.

In the illustrated embodiment, the imaging subsystem 22 is configured for acquiring three-dimensional images of the target tissue mass 16 at a fast rate (i.e., in real-time. Notably, whether images are acquired in real-time will depend on the velocity at which the target tissue mass 16 is expected to move and the error that can be tolerated when tracking the movement of the target tissue mass 16, as will be described in further detail below. For example, if is expected that the target tissue mass 16 may move at 10 cm/sec at a maximum, and the tracking error is less than 1 mm, than it is preferred that the imaging subsystem 22 generate at least 100 images per second. If the target tissue mass 16 moves in accordance with a periodic cycle (e.g., liver motion caused by a cardiac cycle may be 4 cm/sec), the movement of the target tissue mass 16 is more predictable, whereas if the target tissue mass 16 moves in accordance with a non-periodic cycle (e.g., caused by general movement of the patient 14), the movement of the target tissue mass 16 may not be as predictable. Preferably, the rate at which the imaging subsystem 22 acquires images is at least 5 images/second, more preferably, greater than 10 images/second, and most preferably greater than 50 images/second.

In the illustrated embodiment, the imaging subsystem 22 takes the form of a Magnetic Resonance Imaging (MRI) subsystem, which generally comprises a high field magnet 62, a gradient field amplifier 64, a radio frequency (RF) transmitter 66, an RF receiver 68, an MRI controller 70, an MRI processor 72, and a display 74.

The magnet 62 may be integrated with the patient table 56 and includes a region for receiving the patient 14 therein. The magnet 62 provides a static, relatively homogenous magnetic field over the patient 14, as is well known in the art. The gradient field amplifier 64 generates magnetic field gradients that vary the static magnetic field generated by the magnet 62 in a known manner. The RF transmitter 66 generates and transmits RF pulse sequences or other signals over the patient 14 to cause the target tissue mass 16 to emit RF response signals, which may include free induction decay (FID) signals and/or echo signals. In a preferred embodiment, the RF transmitter 66 includes RF coils (not shown) in the magnet 62, and a pulse transmitter (also not shown), which may have a pulse transmitter frequency supplied by a synthesizer (not shown) and/or controlled by the MRI controller 70. The RF receiver 68 senses raw MR response signals. The RF receiver 68 may include a separate set of RF coils (not shown), from the RF transmitter 66. Alternatively, an RF transmitter/receiver (not shown) may be provided that is configured to operate alternately in a transmit mode to transmit RF pulse sequences and a receive mode to sense the MR response signals. Additional receive only or receive/transmit MR imaging coils (not shown) may be placed adjacent the target tissue volume to accomplish a better localized imaging quality.

The MRI controller 70 provides or otherwise controls the timing sequence used to operate the MRI subsystem 22. For example, the timing sequence may include one or more signals instructing the RF transmitter 66 to transmit RF pulse sequences, and/or instructing the RF receiver 68 to listen for MR response signals. For the alternative embodiment wherein an RF transmitter/receiver is provided, the MRI controller 70 may control this operation, for example, by switching the RF coils of the RF transmitter/receiver between the transmit and receive modes. The MRI processor 72, which may include an analog-to-digital converter and/or image processor (both not shown) receives the MR response signals from the RF receiver 68 and generates MR images therefrom in a conventional manner for display on the display 74.

In addition or alternatively, the MRI processor 72 may rapidly acquire temperature-sensitive images of the patient 14. Such temperature-sensitive images may be superimposed on other medical diagnostic images (such as conventional MR images) or provided on separate displays. Preferably, both the target tissue mass 16 and regions heated by the focused ultrasound subsystem 22 may be imaged simultaneously, thereby enabling an operator to verify that the heated region (i.e., the focal zone 34) corresponds to the target tissue mass 16. Additional information on systems and methods for obtaining temperature-sensitive MR images may be found in U.S. Pat. No. 6,559,644, entitled "MRI-Based Temperature Mapping With Error Resolution," and U.S. Pat. No. 6,618,608, entitled "Thermal Imaging of Fat and Muscle Using a Simultaneous Phase and Magnitude Double Echo Sequence," which are expressly incorporated herein by reference.

Notably, in order to quickly adjust the location of the focal zone 34 of the ultrasound energy beam 32 relative to the target tissue mass 16 in response to movements made by internal organs, such as the liver, kidney, spleen, heart, etc., it is desirable that the MR images generated by the MR imager 22 be generated as quickly as possible. To accomplish this, the MR imager 22 preferably acquires images of the target tissue mass 16 using a relatively small scanning window. As such, without adjusting the MR imager 22, the moving target tissue mass 16 may move out of the scanning window of the MR imager 22. To compensate for this, the motion compensation processor 28, which will be described in further detail below, transmits control signals to the MRI controller 70 to adjust the location of the scanning window to correspond with the location of the target tissue mass 16.

Figure 5:
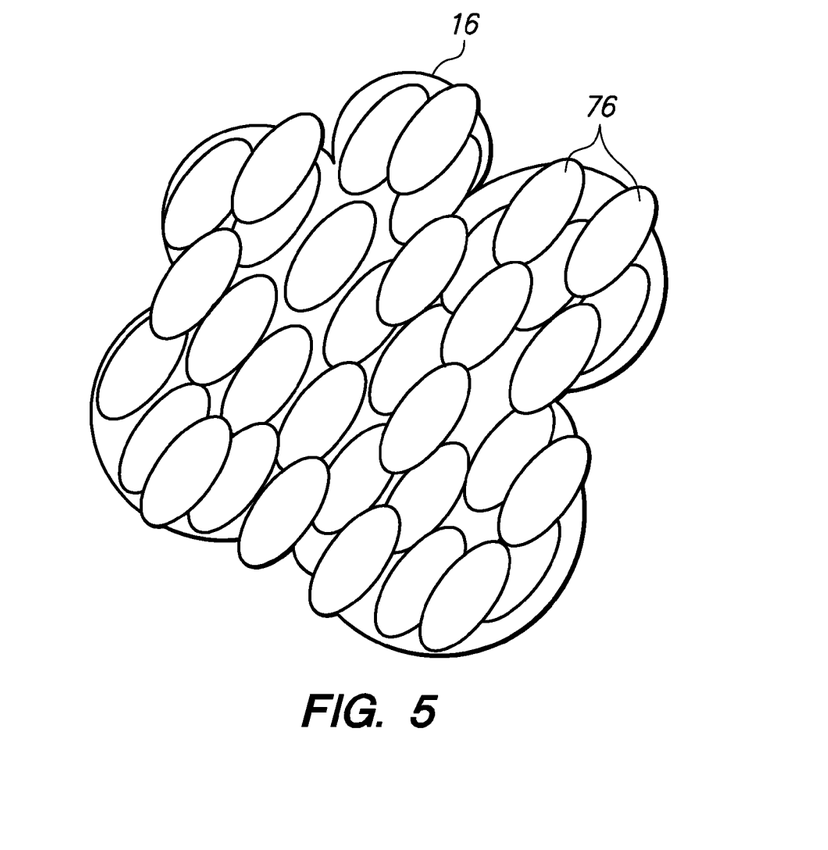
FIG. 5 is a cross-sectional view of a tissue mass treated with a series of sonications performed by the system of FIG. 1.

The planner 24 automatically constructs a treatment plan, which consists of a series of treatment sites represented by thermal dose properties. The purpose of the treatment plan is to ensure complete ablation of the target tissue mass 16 by planning a series of sonications (i.e., distinct applications of the ultrasound beam 32) that will apply a series of thermal doses 76 at various points within the target tissue mass 16, resulting in a composite thermal dose sufficient to treat the entire target tissue mass 16, as illustrated in FIG. 5. The plan will include the afore-described thermal dose properties determined based on default parameters, such as a thermal dose threshold, maximum allowed energy for each thermal dose, thermal dose duration for each treatment site, cooling time between ultrasound applications (sonications), sonication grid density (how much the sonications should overlap), the physical parameters of the transducer 30, the patient anatomy and anatomy constraints.

In order to construct the treatment plan, the planner 24 receives input from the user interface 26. For example, in one implementation, a user specifies the clinical application protocol, i.e., breast, pelvis, eye, prostrate, etc., via the user interface 26. Selection of the clinical application protocol may control at least some of the default parameters. In other implementations, some or all of these parameters are input through the user interface 26 as user specified parameters. Additionally, a user may edit any of the default parameters via the user interface 26. In one implementation, the user interface 26 comprises a Graphical User Interface (GUI). In this case, a user employs a mouse or touch screen to navigate through menus or choices as displayed on the display 74 or another display in order to make the appropriate selections and supply the required information.

To further facilitate construction of the treatment plan, the planner 24 uses images supplied by the MRI subsystem 22 in conjunction with input supplied by the user interface 26. In one implementation, the images are used to define a treatment boundary around the target tissue mass 16, e.g., by tracing a line on the image displayed on the display 74. In the case where the images are three-dimensional, the treatment boundary can be defined in three dimensions. The images may also be used to define obstacle boundaries around tissue that is acoustically reflective (such as gas) or bone and tissue that is otherwise sensitive to thermal exposure.

Figure 6A:
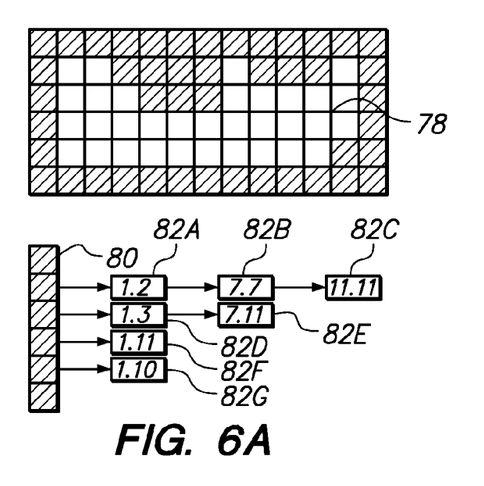
FIGS. 6A-6C are two-dimensional pixel representations of untreated and treated regions of a target tissue mass during a series of sonications performed by the system of FIG. 1.
Figure 6B:
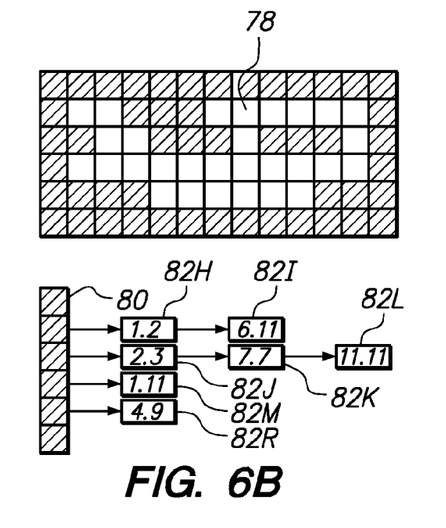
Figure 6C:
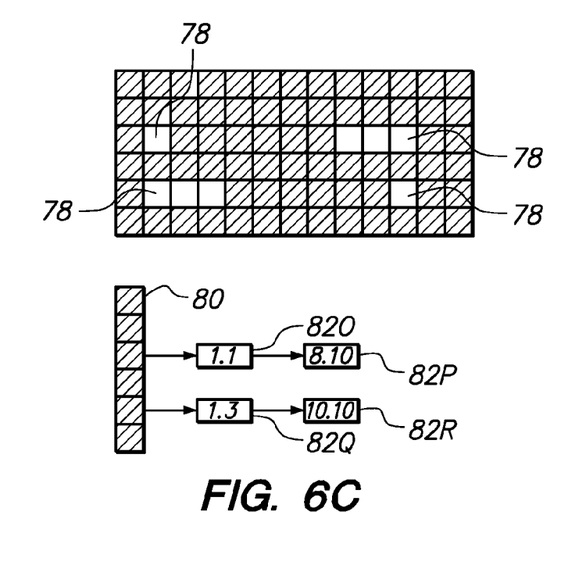

There are several methods that are used to change or update the treatment plan. For example, at the end of each sonication, there may be regions within the target tissue mass 16 that are not covered by accumulated treatment. After each sonication, the treated regions and untreated regions may be taken into account in generating an updated treatment plan. In order to accomplish the tracking of untreated regions, each target tissue mass 16 may be maintained as a two-dimensional linked list of pixel ranges sorted by (y) and then (x) coordinates, as illustrated in FIGS. 6A-6C. Notably, if the target tissue mass 16 is to be represented as a three-dimensional mass, the target tissue mass 16 may be maintained as a three-dimensional linked list of voxel ranges.

As can be seen in FIG. 6A, the target tissue mass 16 is represented as a continuous region 78 of lighter pixels. The pixel distribution is then represented by the data structure 80. This type of representation is called "run-length encoding." The data structure 80 contains linked lists 82 by row indicating the pixels that contain the target tissue mass 16. Thus, for row 1, a list element 82*a* indicates that the pixel range from 1 to 2 contains a portion of the target tissue mass 16, a list element 82*b* indicates that the pixel range from 7 to 7 contains a portion of the target tissue mass 16, and a list element 82*c* indicates that the pixel range from 11 to 11 contains a portion of the target tissue mass 16. For row 2, a list element 82*d* indicates that the pixel range from 1 to 3 contains a portion of the target tissue mass 16, and a list element 82*e* indicates that the pixel range from 7 to 11 contains a portion of the target tissue mass 16. For row 3, a list element 82*f* indicates that the pixel range from 1 to 11 contains a portion of the target tissue mass 16. For row 4, a list element 82*g* indicates that the pixel range from 1 to 10 contains a portion of the target tissue mass 16. It can also be seen that rows 0 and 5 do not contain any portion of the target tissue mass 16. Therefore, these rows in the data structure 80 do not contain any pixel ranges.

Once a sonication is applied, the area of the target tissue mass 16 that is destroyed (the treated region) is presented in the same fashion as the untreated region shown in FIG. 6A, and the treated region is subtracted from the untreated region in order to define the remaining untreated region within the target tissue mass 16. After several sonications, the target tissue mass 16 may be represented as a continuous region 78 of lighter pixels, as illustrated in FIG. 6B. In this case, for row 1, a list element 82*h* indicates that the pixel range from 1 to 2 contains a portion of the target tissue mass 16, and a list element 82*i* indicates that the pixel range from 6 to 11 contains a portion of the target tissue mass 16. For row 2, a list element 82*j* indicates that the pixel range from 2 to 3 contains a portion of the target tissue mass 16, a list element 82*k* indicates that the pixel range from 7 to 7 contains a portion of the target tissue mass 16, and a list element 82*l* indicates that the pixel range from 11 to 11 contains a portion of the target tissue mass 16. For row 3, a list element 82*m* indicates that the pixel range from 1 to 11 contains a portion of the target tissue mass 16. For row 4, a list element 82*n* indicates that the pixel range from 4 to 9 contains a portion of the target tissue mass 16. After several more sonications, the target tissue mass 16 may be represented as discontinuous regions 78 of lighter pixels, as illustrated in FIG. 6C. In this case, for row 2, a list element 82*o* indicates that the pixel range from 1 to 1 contains a portion of the target tissue mass 16, and a list element 82*p* indicates that the pixel range from 8 to 10 contains a portion of the target tissue mass 16. For row 4, a list element 82*q* indicates that the pixel range from 1 to 3 contains a portion of the target tissue mass 16, and a list element 82*r* indicates that the pixel range from 10 to 10 contains a portion of the target tissue mass 16. Further details discussing tracking untreated regions in a target tissue mass are described in U.S. Pat. No. 6,618,620, entitled "Focused Ultrasound System With MRI Synchronization," which is expressly incorporated herein by reference.

The treatment plan or revised treatment plans are passed to the motion compensation processor 28, which calculates the values of the electrical and/or mechanical parameters used by the FUS controller 54 to control the thermal dose properties of the transducer 30 via the electrical driver 48 and the mechanical driver 52. In the case where a treatment boundary and obstacle boundaries are defined, the FUS controller 54 will focus the ultrasound energy beam within the defined treatment boundary of the target tissue mass and/or avoid traversing the defined obstacle boundaries with the ultrasound beam 32.

Significantly, the motion compensation processor 28 is configured for tracking relative movement between the focal zone 34 of the ultrasound energy beam 32 and the target tissue mass 16 in real-time based on the images acquired by the MRI subsystem 22. The relative movement tracked by the motion compensation processor 28 can be non-periodic (for example, random movement of the patient within the MRI subsystem 22). The relative movement tracked by the motion compensation processor 28 can also be periodic (for example, movement of an organ caused by a physiological parameter, such as a respiratory cycle and/or cardiac cycle). Notably, there is a direct correlation between the location of the focal zone 34 of the ultrasound beam 32 and the location of the transducer 30 within the imaging coordinate system. Thus, the motion compensation processor 28 can indirectly track the relative movement between the focal zone 34 of the ultrasound energy beam 32 relative to the target tissue mass 16 by tracking the respective positions of the transducer 30 and the target tissue mass 16 in a common three-dimensional coordinate system (and in particular, the imaging coordinate system) based on the acquired images.

In one implementation, the transducer 30 and the target tissue mass 16 can be located by comparing the currently acquired images of the transducer 30 and the target tissue mass 16 with reference images. For example, the transducer 30 can be located by performing image template matching between the MR image of the transducer 30 and a predefined graphical template that is scaled based on the field of view used, and inferring therefrom the coordinates of the transducer 30 within the image coordinate system. The target tissue mass 16 may be located by performing an image-based maximum correlation algorithm on the currently acquired image of the target tissue mass 16 and a reference image of the target tissue mass 16. In an alternative implementation, image comparison is not performed, but rather the transducer 30 can be located by placing localization elements 31 on the transducer 30. For example, the localization elements 31 may be fiducial elements, in which case artifacts representing the fiducial elements can be located within the MR images in a conventional manner to locate the transducer 30. As another example, the localization elements 31 can be transmitting/emitting/sensing elements that transmit and/or receive signals. By way of non-limiting examples, the transmitting/sensing elements 31 can be MR tracking devices, such as microcoils filled with MR sensitive material, or gradient-based tracking devices, such as microcoils sensitive to gradient magnetic field changes, such that the microcoils (and thus the transducer 30) can be located relative to the MRI subsystem 22. In any event, the determined coordinates of the transducer 30 and the target tissue mass 16 can equal any number, but in one implementation, the coordinates can number six (e.g., x-, y-, and z-rectilinear coordinates, and yaw, pitch, and roll coordinates) or a subset (e.g., four) of these coordinates.

While the motion compensation processor 28 has been described as tracking the position of the focal zone 34 of the ultrasound energy beam 32 indirectly by tracking the location of the transducer 30, the motion compensation processor 28 may alternatively or optionally track the position of the focal zone 34 of the ultrasound energy beam 32 relative to the target tissue mass 16 directly from the images. For example, the focal zone 34 of the ultrasound energy beam can be located by analyzing the optional thermal sensitive images and identifying the "hot spot" or thermal signature in the thermal sensitive image corresponding to the focal zone 34 relative to the target tissue mass 16 in the conventional MR images. In the case where the focal zone 34 is displaced in accordance with a physiological cycle by constructing an atlas of motion with the MR images acquired prior to the treatment period and comparing the respective MR images currently acquired during the treatment period to the images stored in the atlas. Further details discussing this technique are disclosed in Denis de Senneville, B., Mougenot, C., and Moonen, C., Real-Time Adaptive Methods for Treatment of Mobile Organs by MRI-Controlled High-intensity Focused Ultrasound, Magnetic Resonance in Medicine 57:319-330 (2007), which is expressly incorporated herein by reference.

The motion compensation processor 28 uses the tracked relative movement between the focal zone 34 of the ultrasound energy beam 32 and the target tissue mass 16 to continually recalculate or transform the nominal values of the electrical and/or mechanical parameters previously calculated based on the treatment plan generated by the planner 24. These adjusted electrical and/or mechanical parameter values are passed to the FUS controller 54, which automatically adjusts the thermal dose properties of the transducer 30 to maintain the location of the focal zone 34 of the ultrasound energy beam 32 at the target tissue mass 16 or otherwise compensate for the change in the relative position between the transducer 30 and the target tissue mass 16.

As previously discussed, the thermal dose properties of the transducer 30, and in particular the location of the focal zone 34 of the ultrasound energy beam 32, can be changed via control of the electrical driver 48 and mechanical driver 52. Because the thermal dose properties of the transducer 30 should be modified as quickly as possible in order to compensate for relative movement between the transducer 30 and the target tissue mass 16 in real-time, it is preferred that the location of the focal zone 34 of the ultrasound energy beam 32 be adjusted, at least in part, via control of the electrical driver 48, which is faster than the mechanical driver 52.

As an alternative to, or as an adjunct to, compensating for the relative movement between the transducer 30 and the target tissue mass 16, the adjusted electrical and/or mechanical parameter values are passed to the planner 24, such that the treated and untreated regions of the target tissue mass 16 can be more accurately tracked. That is, by knowing the relative position between the focal zone 34 of the ultrasound energy beam 30 during each sonication, the linked lists 82 can be more accurately generated.

Figure 7:
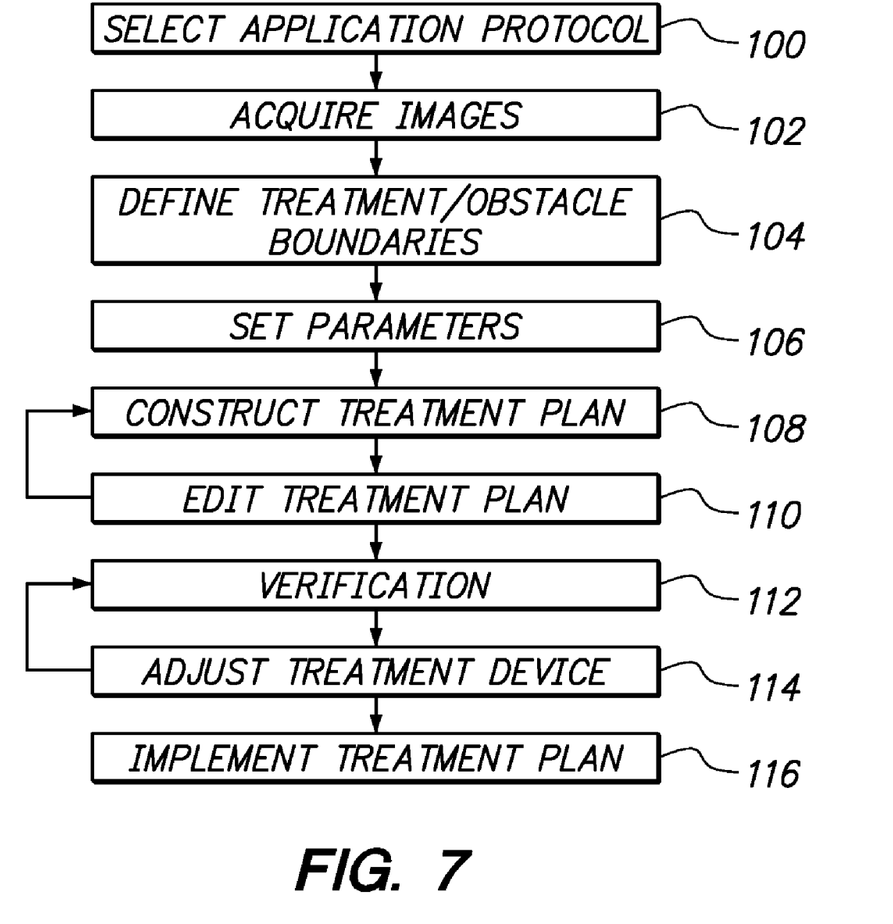
FIG. 7 is a flow diagram illustrating a method of operating the system of FIG. 1 to treat a target tissue mass within the interior region of a patient.

Having described the structure and function of the system 10, its operation in treating the target tissue mass 16 will now be described with further reference to FIG. 7. Initially, the system operator 12 selects an appropriate clinical application protocol via the user interface 26, after which the planner 24 or the FUS controller 54 will select or change the default parameters (step 100). After the clinical application is selected, relevant MR images of the target tissue mass 16 are acquired by the MRI subsystem 22 (step 102). Next, the system operator 12 uses the acquired MR images to define the treatment and obstacle boundaries via the user interface 26 (step 104). The system operator 12 may then enter additional default parameters or modify previously defined default parameters via the user interface 26 (step 106). The planner 24 then automatically constructs the treatment plan based on the defined treatment and obstacle boundaries and the default parameters (step 108). Next, the system operator 12 may edit the treatment plan via the user interface 26, e.g., by adding or deleting treatment boundaries and/or obstacle boundaries, changing the location of some or all of the treatment sites, or changing thermal dose properties (step 110). If the treatment plan is edited, the process returns to step 108 where the treatment plan is reconstructed/recalculated. Once the treatment plan is set, proper registration of the system 10 with regard to the position of the focal zone 34 relative to the target tissue mass 16 is verified (step 112). This verification step can comprise performing a low energy thermal dose at a predefined site within the target tissue mass 16 and generating a thermally sensitive image in order to ensure that the focal zone 34 is located within the target tissue mass 16. If the system 10 is not properly registered, the FUS controller 54 may be operated via the user interface 26 to adjust the mechanical position of the transducer 30 via the mechanical driver 52, which mechanical position can then be set as a "home" position (step 114). The process can then return to step 112 to again verify the registration of the system 10. Once verification is complete, the treatment plan is implemented (step 116).

During implementation step of the treatment plan, a sonication can be performed via operation of the focused ultrasound subsystem 18 while MRI images are acquired by the MRI subsystem 22. The MRI images may be temperature sensitive images sequences as each step of the treatment plan is implemented. These images will illustrate the actual thermal dose distribution resulting from each successive thermal dose. Significantly, during implementation of the treatment plan, the motion compensation processor 28 tracks the relative position between the focal zone 34 of the ultrasound energy beam 30 and the target tissue mass 16 and calculates the electrical and/or mechanical parameters necessary to maintain the focal zone 34 at the desired site of the target tissue mass 16, and the FUS controller 54 controls the electrical driver 48 and/or the mechanical driver 52 to adjust the thermal dose parameters of the transducer 30. The motion compensation processor 28 may also track the treated and untreated regions of the target tissue mass 16 based on the tracked relative position between the focal zone 34 and the target tissue mass 16.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. An image-guided therapy system for applying thermal treatment to a target tissue mass notwithstanding non-periodic relative motion between the target tissue mass and a thermal treatment device, the system comprising:
   a thermal treatment device configured for transmitting a therapeutic energy beam;
   an imaging device configured for acquiring images of the target tissue mass and the thermal treatment device;
   a processor configured for tracking respective positions of the thermal treatment device and the target tissue mass in a common coordinate system based on the acquired images of the target tissue mass and the thermal treatment device, and indirectly tracking a focus position based on (i) the respective positions of the thermal treatment device and the target tissue and (ii) a correlation between the focus position and the position of the treatment device; and
   a controller configured for controlling the thermal treatment device to focus the energy beam on the target tissue mass, at a distance from the thermal treatment device, the controller being responsive to the processor so as to automatically maintain the focus of the energy beam on the target tissue mass notwithstanding the non-periodic relative motion.

2. The system of claim 1, wherein the thermal treatment device is an external thermal treatment device configured for transcutaneously transmitting the energy beam into the patient.

3. The system of claim 1, wherein the thermal treatment device is an ultrasound transducer, and the energy beam is an ultrasound energy beam.

4. The system of claim 1, wherein the imaging device is a magnetic resonance imaging (MRI) device.

5. The system of claim 1, wherein the thermal treatment device and the imaging device are the same device.

6. The system of claim 1, wherein the common coordinate system is a three-dimensional 7. The system of claim 1, wherein the processor is configured for tracking the respective positions of the thermal treatment device and the target tissue mass by analyzing fiducial markers associated with one or both of the thermal treatment device and the target tissue mass within the acquired images.

8. The system of claim 1, wherein the processor is configured for tracking the respective positions of the thermal treatment device and the target tissue mass by transmitting or receiving signals to or from a localization element associated with one or both of the thermal treatment device and the target tissue mass.

9. The system of claim 1, wherein the processor is configured for tracking the respective positions of the thermal treatment device and the target tissue mass by comparing the acquired images with one or more reference images.

10. The system of claim l, further comprising a user interface configured for allowing a system operator to define a treatment boundary of the target tissue mass using the acquired images, wherein the controller is configured for automatically controlling the thermal treatment device to focus the energy beam within the defined treatment boundary of the target tissue mass.

11. The system of claim 1, wherein the processor is configured for tracking treated regions and untreated regions of the target tissue mass based on the tracked positions of the thermal treatment device and the target tissue mass.

12. The system of claim 3, wherein the ultrasound transducer is a phased-array transducer.

13. The system of claim 12, further comprising an electrical driver coupled to the phased-array ultrasound transducer, the controller controlling a location of the focus of the energy beam via the electrical driver.

14. The system of claim 1, wherein the imaging device acquires images within a scanning window, a location of the scanning window being adjusted based on control signals from the processor to correspond with a location of the target tissue mass.

* * * * *

UNITED STATES PATENT AND TRADEMARK OFFICE
CERTIFICATE OF CORRECTION

| | | |
|---|---|---|
| PATENT NO. | : 8,251,908 B2 | |
| APPLICATION NO. | : 11/865662 | |
| DATED | : August 28, 2012 | |
| INVENTOR(S) | : Jacob Vortman et al. | |

It is certified that error appears in the above-identified patent and that said Letters Patent is hereby corrected as shown below:

In the Claims:

Column 15 Claim 6, line 17, should read:
--system is a three-dimensional coordinate system.--

Signed and Sealed this
Thirteenth Day of November, 2012

David J. Kappos
*Director of the United States Patent and Trademark Office*